(12) United States Patent
Nagase et al.

(10) Patent No.: US 11,109,837 B2
(45) Date of Patent: Sep. 7, 2021

(54) PORTABLE ULTRASOUND IMAGE DIAGNOSTIC APPARATUS

(71) Applicant: KONICA MINOLTA, INC., Tokyo (JP)

(72) Inventors: Hisayoshi Nagase, Hachioji (JP); Takahiko Shiraishi, Kunitachi (JP); Tatsushi Chihara, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 1017 days.

(21) Appl. No.: 14/539,680

(22) Filed: Nov. 12, 2014

(65) Prior Publication Data

US 2015/0141835 A1 May 21, 2015

(30) Foreign Application Priority Data

Nov. 20, 2013 (JP) .............................. JP2013-239506
Dec. 25, 2013 (JP) .............................. JP2013-266804

(51) Int. Cl.
*A61B 8/00* (2006.01)

(52) U.S. Cl.
CPC .......... *A61B 8/4427* (2013.01); *A61B 8/4405* (2013.01); *A61B 8/4433* (2013.01); *A61B 8/4411* (2013.01)

(58) Field of Classification Search
None
See application file for complete search history.

(56) References Cited

U.S. PATENT DOCUMENTS

| 5,168,426 A | 12/1992 | Hoving et al. |
| 6,540,685 B1 * | 4/2003 | Rhoads ................... A61B 8/00 600/459 |
| 6,980,419 B2 | 12/2005 | Smith et al. |
| 7,113,397 B2 * | 9/2006 | Lee ........................ G06F 1/162 248/919 |

(Continued)

FOREIGN PATENT DOCUMENTS

| JP | H05035739 A | 2/1993 |
| JP | 2004118386 A * | 4/2004 |

(Continued)

OTHER PUBLICATIONS

Japanese Office Action (and English translation thereof) dated May 16, 2017 issued in counterpart Japanese Application No. 2013-239506.

(Continued)

*Primary Examiner* — Yi-Shan Yang
(74) *Attorney, Agent, or Firm* — Holtz, Holtz & Volek PC

(57) ABSTRACT

A portable ultrasound image diagnostic apparatus is shown. The apparatus includes an ultrasound probe and a hinge. The ultrasound probe transmits and receives ultrasound. The hinge connects a first housing and a lower edge portion of a second housing including a display panel so that the second housing is overlapped on the first housing to fold the portable ultrasound image diagnostic apparatus. The hinge is provided on an upper face of the first housing in a near side than a center. The second housing is rotated to a far side of the first housing with a horizontal axis of the hinge as a supporting axis to fold the portable ultrasound image diagnostic apparatus.

27 Claims, 14 Drawing Sheets

(56) References Cited

U.S. PATENT DOCUMENTS

| | | | |
|---|---|---|---|
| 7,699,776 B2 | 4/2010 | Walker et al. | |
| 8,435,183 B2* | 5/2013 | Barnes | A61B 5/0402 |
| | | | 600/437 |
| 8,749,964 B2 | 6/2014 | Kimura et al. | |
| 9,597,057 B2 | 3/2017 | Ichimura | |
| 2005/0107142 A1* | 5/2005 | Soejima | H04M 1/0247 |
| | | | 455/575.3 |
| 2005/0154303 A1* | 7/2005 | Walker | G01S 7/52061 |
| | | | 600/443 |
| 2007/0081304 A1* | 4/2007 | Takeguchi | G06F 1/162 |
| | | | 361/679.27 |
| 2010/0121195 A1* | 5/2010 | Kang | A61B 8/00 |
| | | | 600/459 |
| 2011/0235251 A1* | 9/2011 | Kimura | A61B 8/462 |
| | | | 361/679.01 |
| 2012/0162889 A1* | 6/2012 | Han | G06F 1/162 |
| | | | 361/679.09 |
| 2013/0201625 A1* | 8/2013 | Liang | G06F 1/1624 |
| | | | 361/679.55 |
| 2013/0235420 A1* | 9/2013 | Nihashi | G07G 1/0018 |
| | | | 358/1.15 |
| 2013/0329351 A1* | 12/2013 | Lin | G06F 1/1624 |
| | | | 361/679.27 |
| 2015/0038841 A1 | 2/2015 | Ichimura | |
| 2015/0245816 A1* | 9/2015 | Poland | G01S 15/899 |
| | | | 600/447 |
| 2015/0289841 A1* | 10/2015 | Brusaca | A61B 8/4405 |
| | | | 600/437 |

FOREIGN PATENT DOCUMENTS

| | | | | |
|---|---|---|---|---|
| JP | 2006230015 A | 8/2006 | | |
| JP | 2007102075 A | 4/2007 | | |
| JP | 2009066923 A | 4/2009 | | |
| JP | 2010162107 A | 7/2010 | | |
| JP | 2010240072 A | 10/2010 | | |
| JP | 2013198805 A | 10/2013 | | |
| JP | WO 2013145866 A1 * | 10/2013 | | A61B 8/4427 |
| WO | 2010073571 A1 | 7/2010 | | |
| WO | 2010150541 A1 | 12/2010 | | |
| WO | 2012132506 A1 | 10/2012 | | |
| WO | 2013145866 A1 | 10/2013 | | |

OTHER PUBLICATIONS

Japanese Office Action (and English translation thereof) drafted Apr. 26, 2017 in counterpart Japanese Application No. 2013-266804.
Japanese Office Action (and English language translation thereof) dated Dec. 18, 2018 issued in Japanese Application No. 2017-253975.
Japanese Office Action (and English language translation thereof) dated Jul. 7, 2020 issued in Japanese Application No. 2019-062363.

* cited by examiner

PORTABLE ULTRASOUND IMAGE DIAGNOSTIC APPARATUS

BACKGROUND

Field of the Invention

The present invention relates to a portable ultrasound image diagnostic apparatus.

Description of Related Art

Conventionally, an ultrasound image diagnostic apparatus is known, where ultrasound is transmitted and received between a sample such as a live body, etc. with an ultrasound probe, ultrasound image data is generated based on a signal obtained from the received ultrasound, and an ultrasound image based on the above is displayed on an image display apparatus. According to ultrasound image diagnosis using such apparatus, condition of heartbeat, movement of a fetus, etc. can be obtained in real time with a simple operation of simply touching the surface of the sample with the ultrasound probe. Such diagnosis is non-invasive and high in safety, and therefore can be repeatedly performed.

Moreover, recently a small and portable ultrasound image diagnostic apparatus is used and diagnosis has become possible in places other than medical facilities such as hospitals.

In such portable ultrasound image diagnostic apparatuses, for example, a back edge of a first housing provided with an operation unit operable by a user and a bottom edge of a second housing including a display panel are connected by a hinge, and after the ultrasound image diagnosis is finished, the second housing is rotated toward the near side with the hinge as the supporting axis so that the apparatus can be stored (for example, U.S. Pat. No. 6,980,419).

As described above, since the portable ultrasound image diagnostic apparatus is small, there is an advantage that the apparatus can be placed anywhere when the ultrasound image diagnosis is performed.

However, according to the portable ultrasound image diagnostic apparatus as shown in U.S. Pat. No. 6,980,419, since the display panel is provided in the far side of the apparatus, when the apparatus is provided in a position higher than the line of view of the user such as the physician or the patient, and the ultrasound diagnostic image is viewed from below the apparatus while the diagnosis is performed, the first housing blocks the view, and the display panel becomes difficult to see in ultrasound image diagnosis.

SUMMARY

The present invention has been made in consideration of the above problems, and it is one of main objects to provide a portable ultrasound image diagnosis apparatus in which the visibility of the display panel is enhanced.

In order to achieve the above-described objects, according to an aspect of the present invention, there is provided a portable ultrasound image diagnostic apparatus including:

an ultrasound probe which transmits and receives ultrasound; and a hinge which connects a first housing and a lower edge portion of a second housing including a display panel so that the second housing is overlapped on the first housing to fold the portable ultrasound image diagnostic apparatus, the hinge provided on an upper face of the first housing in a near side than a center, wherein, the second housing is rotated to a far side of the first housing with a horizontal axis of the hinge as a supporting axis to fold the portable ultrasound image diagnostic apparatus.

Preferably, in the portable ultrasound image diagnostic apparatus, the hinge is a biaxial hinge further including a vertical axis vertical to the horizontal axis, and the second housing can be rotated with the vertical axis as a supporting axis.

Preferably, in the portable ultrasound image diagnostic apparatus, the display panel is a touch panel.

Preferably, the portable ultrasound image diagnostic apparatus further includes, a sliding member where the hinge is attached; and a guiding unit which guides the sliding member in a front and back direction of the upper face of the first housing.

Preferably, the portable ultrasound image diagnostic apparatus further includes, an operating region provided with at least one operating member which can be operated by a user in a near side than the hinge of the first housing; and a gripping portion to grip a front edge portion of the first housing in which a gripping hole where a hand of the user can be inserted is provided in the operating region.

Preferably, in the portable ultrasound image diagnostic apparatus, the second housing is rotatable by a rotating shaft with respect to the first housing in an opened state; and a damage preventing body in a ring shape is provided in an outer peripheral portion of the rotating shaft, wherein part of the rotating shaft is inserted inside the first housing and the damage preventing body comes into contact with an outer peripheral portion of the second housing when the second housing is tilted from a state other than a closed position.

Preferably, in the portable ultrasound image diagnostic apparatus, a cutout portion is provided in the damage preventing body in the closed position of the second housing.

Preferably, in the portable ultrasound image diagnostic apparatus, a straight line portion is provided in an edge of the second housing on a side where the first housing is and the cutout portion has a shape where the straight line portion does not come into contact with the cutout portion when the second housing is closed.

Preferably, in the portable ultrasound image diagnostic apparatus, the cutout portion has a straight line shape.

Preferably, in the portable ultrasound image diagnostic apparatus, the damage preventing body is formed from a material softer than an outer peripheral frame provided in the outer peripheral portion of the second housing.

Preferably, in the portable ultrasound image diagnostic apparatus, the damage preventing body is formed from rubber or synthetic resin and the outer peripheral frame of the second housing is formed from metal.

Preferably, in the portable ultrasound image diagnostic apparatus, a storing portion of the hinge is provided in an edge of the second housing on a side where the first housing is.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

First Embodiment

Figure 1:
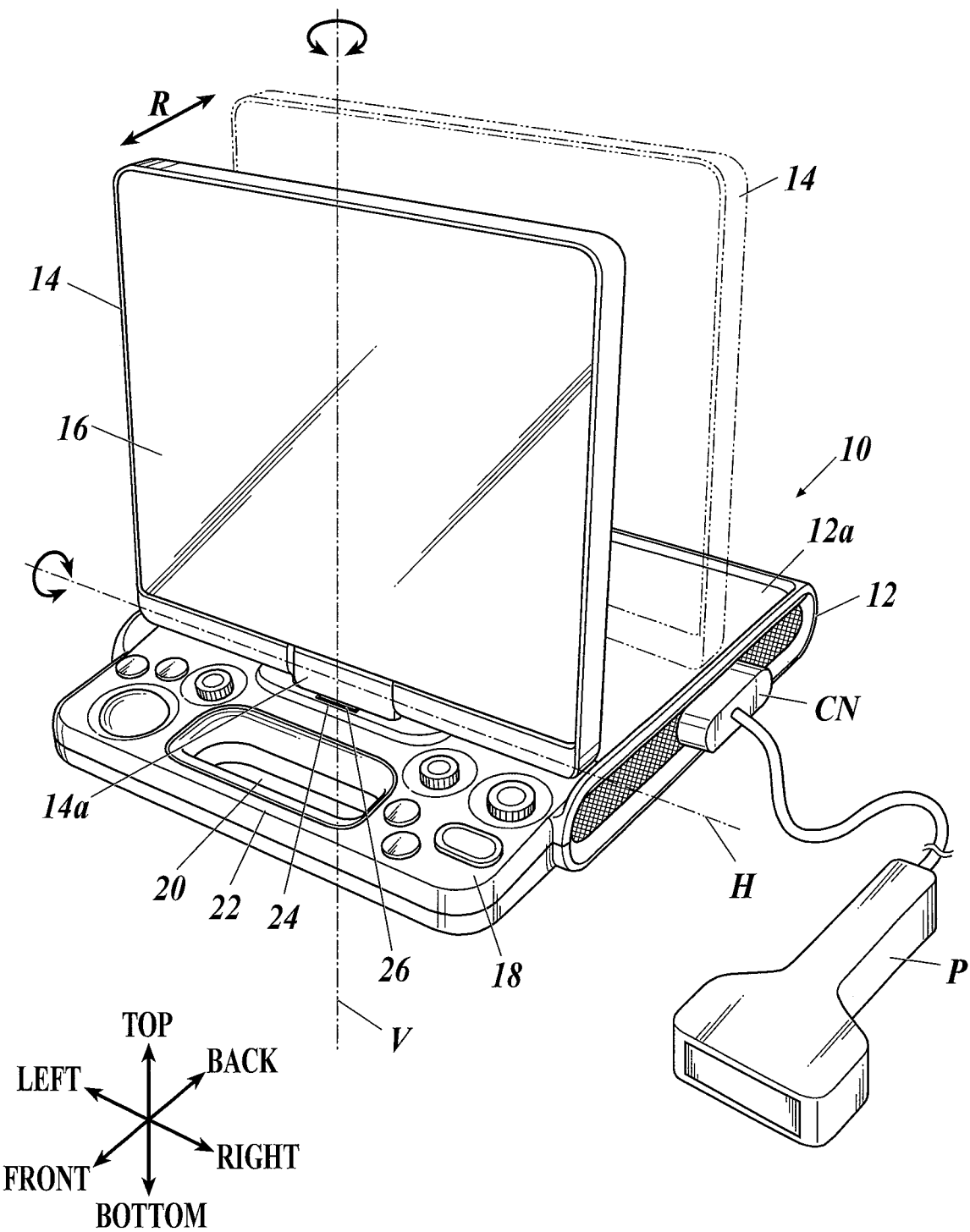
FIG. 1 is a perspective view showing an exterior appearance of the ultrasound image diagnostic apparatus of the first embodiment.

Below, the ultrasound image diagnostic apparatus of the first embodiment of the present invention is described with reference to FIG. 1 to FIG. 7. However, the scope of the invention is not limited to the illustrated examples. In the description below, the same reference numerals are applied to the same functions and configurations and the description is omitted.

Figure 2:
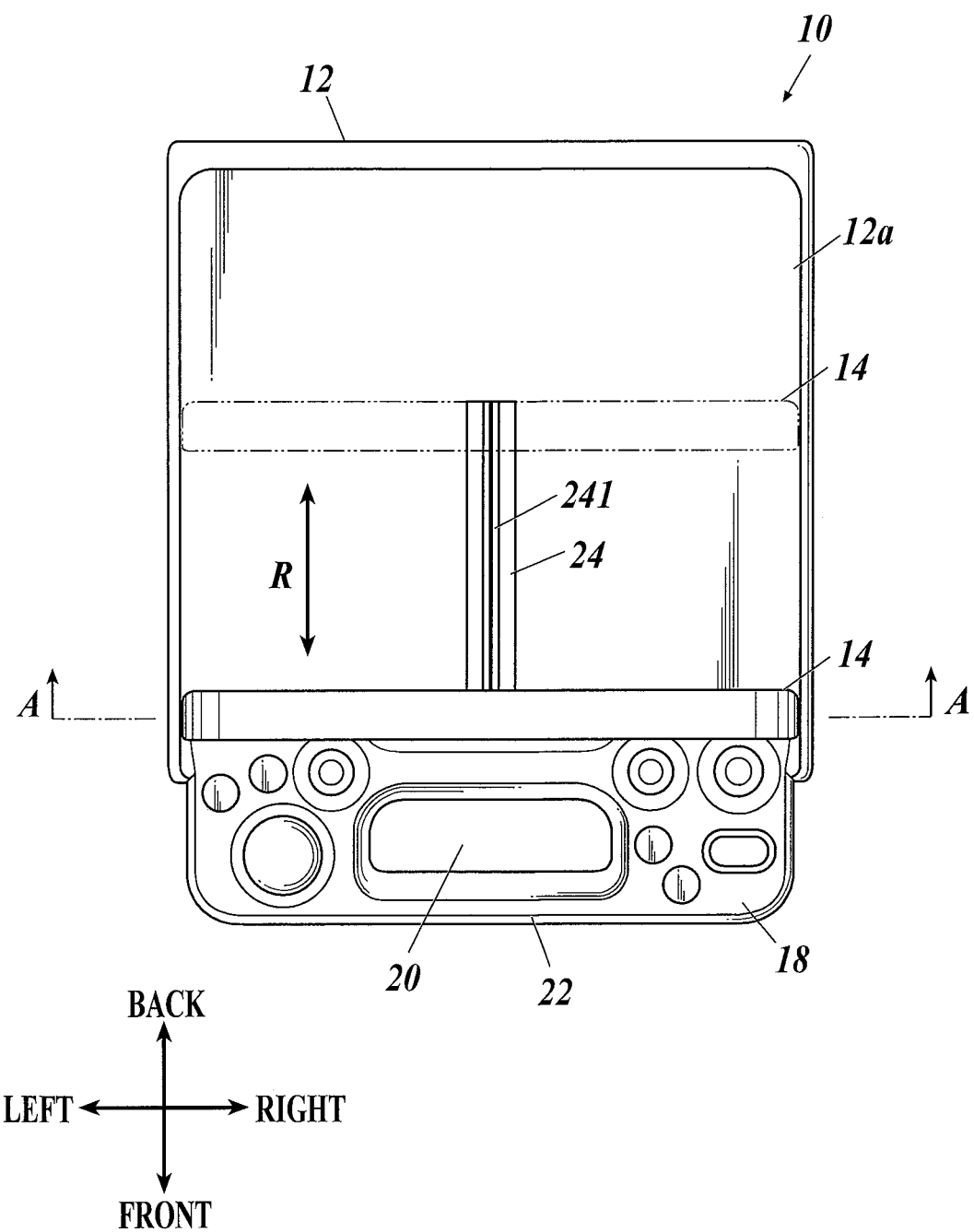
FIG. 2 is a planar view showing an exterior appearance of the ultrasound image diagnostic apparatus.

As shown in FIG. 1 and FIG. 2, the ultrasound image diagnostic apparatus 10 as the portable ultrasound image diagnostic apparatus includes a box shaped apparatus main body 12 as a first housing, and a lid 14 as a second housing including a display panel 16 on a front face. For example, the apparatus main body 12 is formed from a magnesium alloy and inside, the apparatus main body 12 stores an electronic circuit substrate including electronic components such as a CPU (Central Processing Unit) (not shown). The lid 14 is formed in a size to match with the apparatus main body 12 from a planar view when folded. For example, the display panel 16 is a touch panel including a display apparatus such as a LCD (Liquid Crystal Display), or Organic EL (Organic Luminescence) Display, and a position input apparatus on the display screen of the display apparatus. For example, the position input apparatus is a pressure sensitive type (resistive film type) where transparent electrodes are provided in a matrix shape on the display screen. The XY coordinate of the pressure point pressed on the screen with the finger is detected with a voltage value, and the detected position signal is output as the operation signal. The position input apparatus is not limited to a pressure sensitive type and a suitable type selected from various types such as capacitance type can be applied to the present embodiment. The display panel 16 is not limited to a touch panel, and can be a display apparatus which only has a displaying function.

In the description of the present embodiment below, left and right, front and back, and top and bottom are based on the user of the ultrasound image diagnostic apparatus 10 facing the display panel 16.

Figure 3:
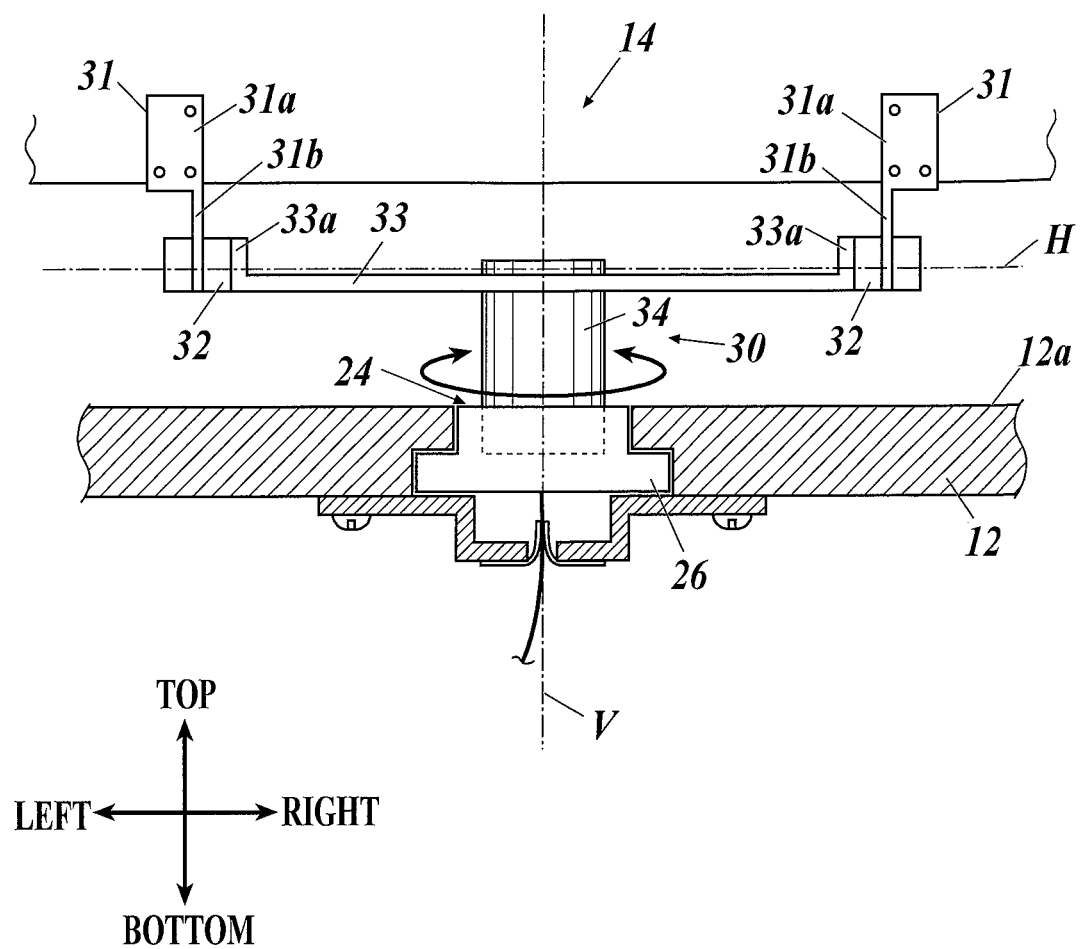
FIG. 3 is a partial enlarged image of the hinge.
Figure 4:
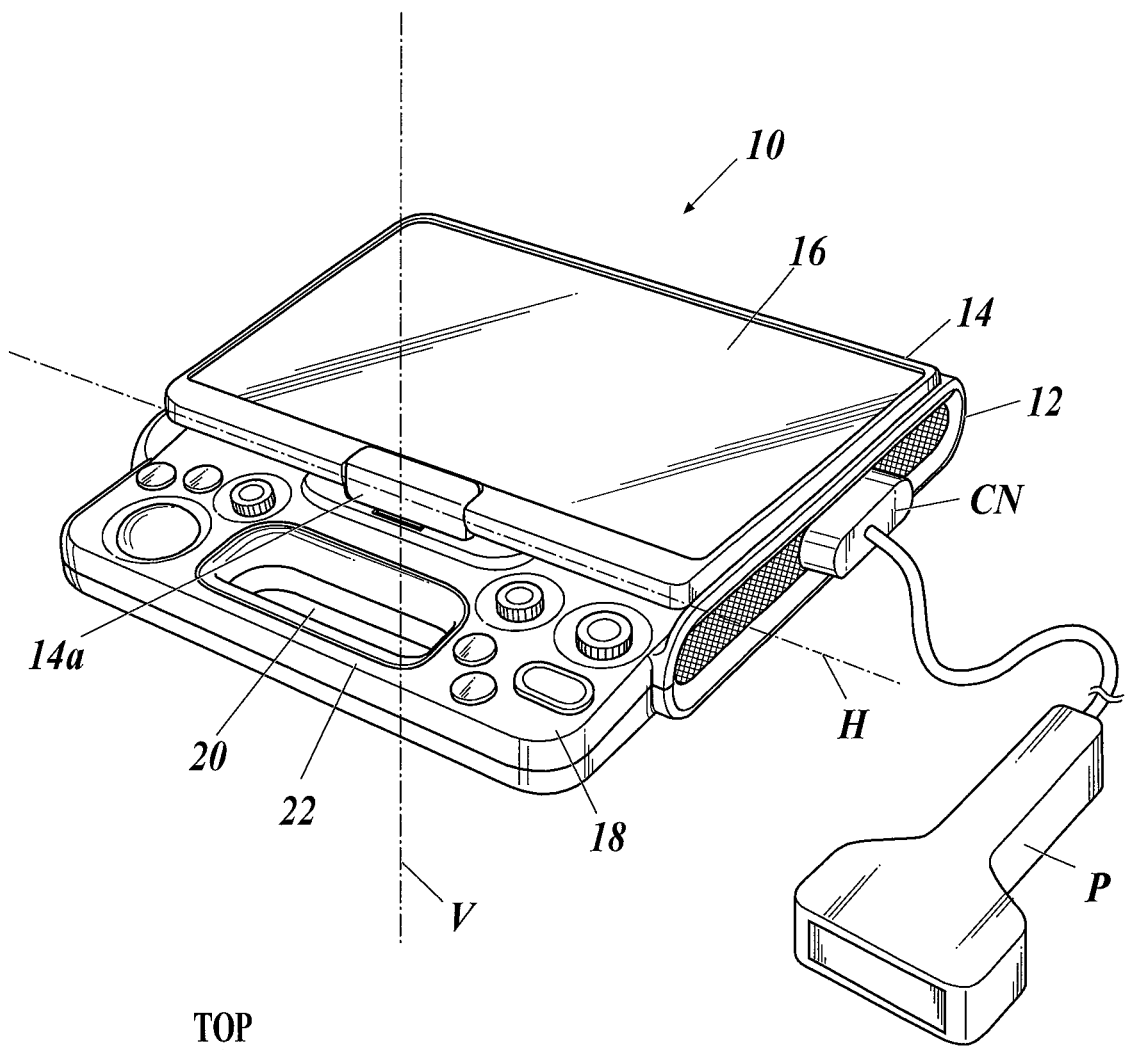
FIG. 4 is a perspective view showing a state where the ultrasound image diagnostic apparatus is folded.
Figure 4:
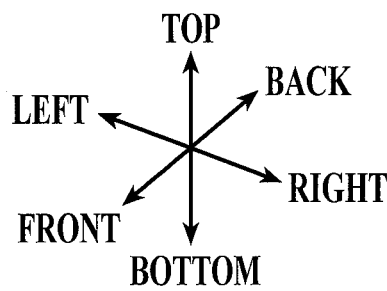
Figure 5:
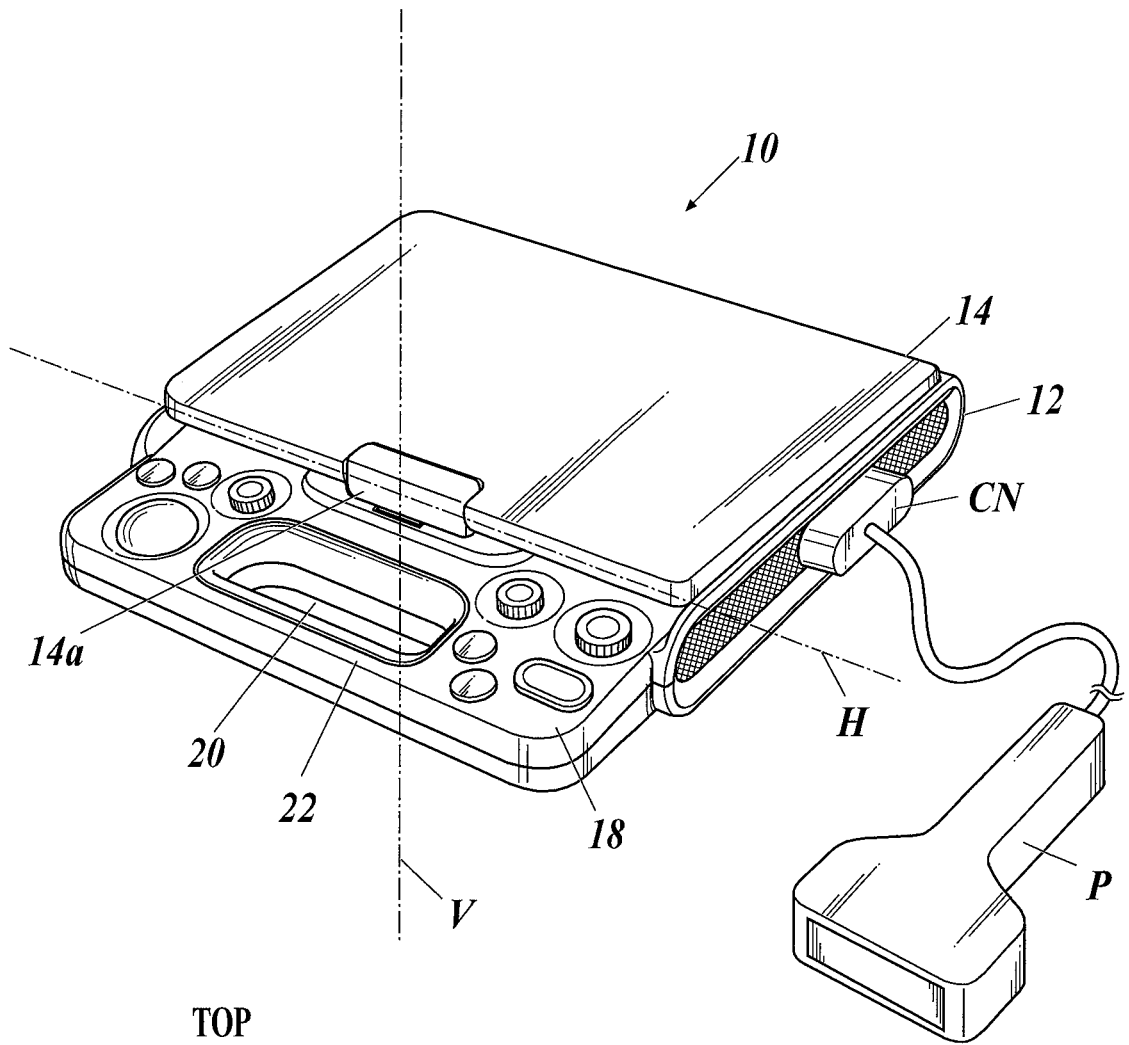
FIG. 5 is a perspective view showing a state where the ultrasound image diagnostic apparatus is folded.

According to the present embodiment, at a position to the front (near side) than the center of an upper face 12a of the apparatus main body 12, the upper face 12a of the apparatus main body 12 and a lower edge portion of the lid 14 are connected with a hinge 30 (see FIG. 3) which is covered with a cover 14a. The hinge 30 is a biaxial hinge, and is able to rotate the lid 14 with respect to the apparatus main body 12 around a horizontal axis H and a vertical axis V as shown in FIG. 1. Therefore, for example, when the lid 14 is tilted backward (far side) from the state shown in FIG. 1 with the horizontal axis H as the supporting axis, as shown in FIG. 4, the lid 14 and the apparatus main body 12 overlap with each other with the back face of the lid 14 and the upper face 12a of the apparatus main body 12 facing each other. With this, the ultrasound image diagnostic apparatus 10 can be folded. In other words, the ultrasound image diagnostic apparatus 10 is folded so that the display panel 16 is exposed upward. Moreover, when the lid 14 is rotated from the state shown in FIG. 1 with the vertical axis V as the supporting axis so that the display panel 16 faces backward (in other words, the back face of the lid 14 faces forward), and then the lid 14 is tilted backward with the horizontal axis H as the supporting axis, as shown in FIG. 5, the display panel 16 and the upper face 12a of the apparatus main body 12 face each other, and the lid 14 and the apparatus main body 12 overlap with each other. With this, the ultrasound image diagnostic apparatus 10 can be folded.

The specific configuration of the hinge 30 is described with reference to FIG. 3. FIG. 3 is a partial enlarged diagram of the hinge 30 viewed from the front side. Actually, the hinge 30 is covered with the cover 14a, and therefore cannot be viewed from outside.

As shown in FIG. 3, for example, the hinge 30 includes a rotating shaft 34, a horizontal arm 33, a torque limiter 32, and an attaching plate 31. The hinge 30 is attached to a sliding base 26 engaged to an upper face 12a of the apparatus main body 12.

The rotating shaft 34 is rotatably supported with the vertical axis V as the supporting axis in the center of the upper face of the sliding base 26. The torque limiter (not shown) is provided in the supporting portion of the rotating shaft 34 of the sliding base 26 and is provided to rotate around the sliding base 26 when the rotating force with a predetermined torque is provided on the rotating shaft 34.

The upper edge portion of the rotating shaft 34 is fixed to the horizontal arm 33 extending in the left and right direction. In other words, the horizontal arm 33 is able to rotate with the vertical axis V as the axis together with the rotating shaft 34. A disk shaped flange 33a extending upward is formed as one with the horizontal arm 33 at each edge of the horizontal arm 33. The torque limiter 32 in a cylinder shape to match the outer side face of the flange 33a is fixed to each outer side face of the flange 33a.

The torque limiter 32 rotatably supports the attaching plate 31 with the horizontal axis H as the supporting axis. The torque limiter 32 allows the attaching plate 31 to rotate when the rotating force of a predetermined torque is applied to the attaching plate 31.

The attaching plate 31 includes an arm 31b attached to the torque limiter 32 and a flat plate shaped attaching portion 31a formed as one with the arm 31b at the tip of the arm 31b. The attaching portion 31a includes a plurality of screw holes and can be held to the lid 14 with screws.

Since the present embodiment has the above configuration, the lid 14 can be rotated around the vertical axis V and the horizontal axis H and then can be held in the rotated position.

According to the present embodiment, as described above, a biaxial hinge is applied as the hinge 30. As for the horizontal axis H, a rotatable single axis hinge can be applied.

As shown in FIG. 1, a terminal (not shown) is provided on a right side face of the apparatus main body 12, and the terminal is configured so that a connector CN of an ultrasound probe P can be connected. With this, the ultrasound probe P transmits ultrasound (transmitting ultrasound) to a sample such as a live body (not shown), and the reflecting ultrasound (echo) reflected from the sample can be received. In other words, the ultrasound image diagnostic apparatus 10 transmits a driving signal as an electric signal to the ultrasound probe P and the ultrasound probe P transmits the transmitting ultrasound to the sample. Then, a receiving signal as an electric signal generated in the ultrasound P according to the reflecting ultrasound from the sample is received by the ultrasound probe P. Based on the above, the ultrasound image diagnostic apparatus is able to image an internal state of the sample as an ultrasound image.

An operating region 18 is formed on a near side than the hinge 30 on the upper face 12a of the apparatus main body 12, and at least one operating member such as a trackball, a dial, a button, etc. which can be operated by the user is provided on the operation region 18. A substantially square shaped gripping hole 20 is open in the substantial center of the operating region 18 and the hand of the user can be inserted through the gripping hole 20. In other words, the operating region 18 is provided so that the operating member is provided surrounding the gripping hole 20. Then, the user is able to grip a gripping portion 22 formed in front of the gripping hole 20 with the hand inserted through the gripping hole 20. According to such configuration, the ultrasound image diagnostic apparatus 10 can be easily transported with one hand. According to the present embodiment, the gripping hole 20 is in the operating region 18, however, the gripping portion 22 can be projected from the front edge of the apparatus main body 12. Moreover, the gripping hole 20 does not need to be provided. Moreover, the gripping portion 22 can also have the function as a hand rest when the user operates the touch panel. With this, the user can easily operate the touch panel, and the exhaustion of the operator can be reduced.

A sliding groove 24 extending in the front and back direction is formed from the center of the upper face 12a of the apparatus main body 12 to the operating region 18. The sliding groove 24 guides the sliding base 26 with the hinge 30 attached to slide in the front and back direction. Therefore, the lid 14 is able to slide in the front and back direction (direction shown with arrow R in FIG. 1 and FIG. 2) along the sliding groove 24 with respect to the apparatus main body 12. As a result, the lid 14 can change the position between the position shown with a solid line and the position shown with a broken line in FIG. 1 and FIG. 2.

Figure 6:
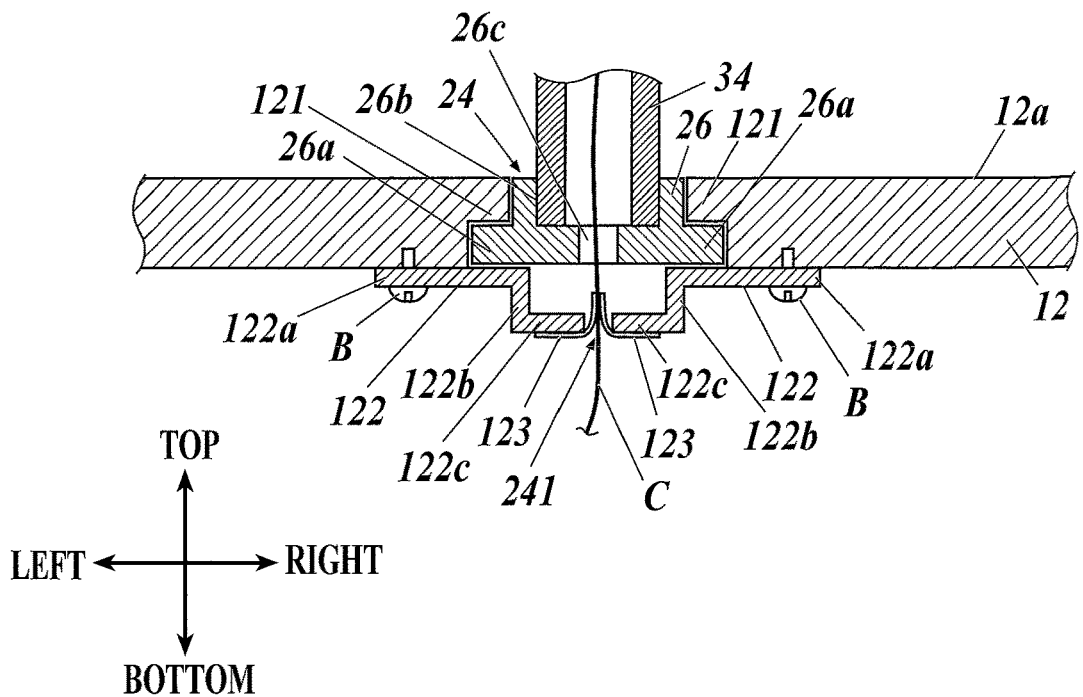
FIG. 6 is an enlarged diagram of a cross-sectional surface A-A in FIG. 2.
Figure 7:
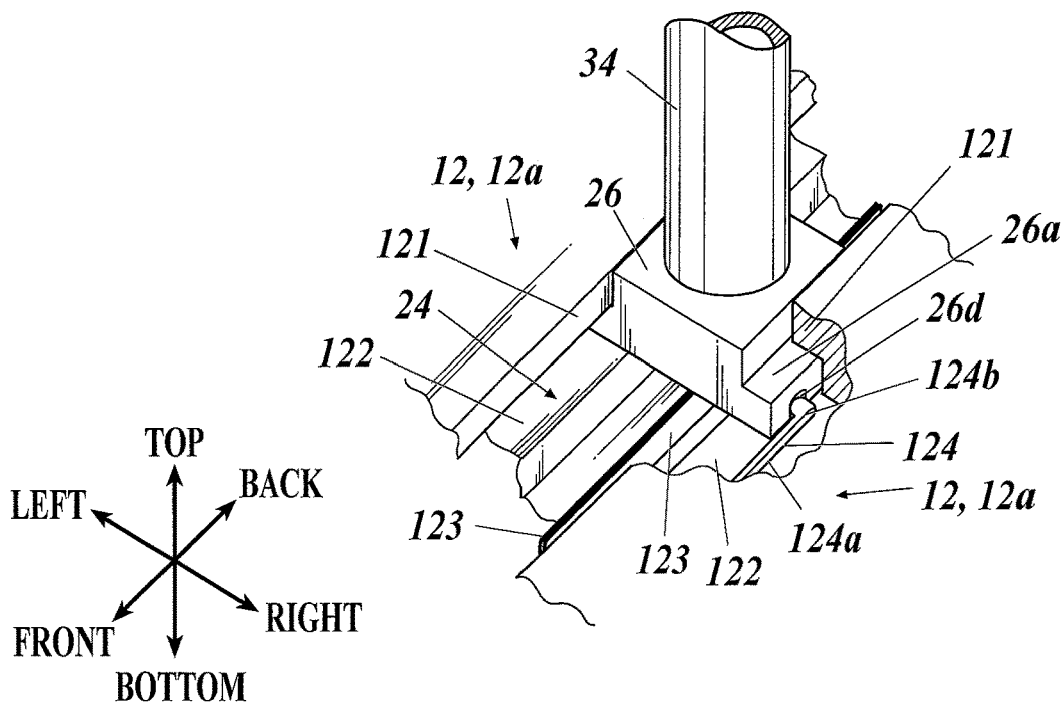
FIG. 7 is a partial enlarged diagram of a sliding base.

Here, the configuration to enable the lid 14 to slide with respect to the apparatus main body 12 is specifically described with reference to FIG. 6 and FIG. 7. FIG. 6 is an enlarged diagram of the cross section of line A-A in FIG. 2 enlarging the portion of the sliding base 26. FIG. 7 is a partial enlarged perspective diagram enlarging the portion of the sliding base 26. In FIG. 7, the diagram is illustrated as if a portion of the upper face 12a of the apparatus main body 12 is ruptured.

As shown in FIG. 6 and FIG. 7, a pair of flanges 121 are provided projected toward each other on the upper face side of the upper face 12a of the apparatus main body 12. With this, the cutout portion in a convex shape viewed from the cross section forms the sliding groove 24 as the guiding portion extending in the front and back direction. Then, a pair of supporting members 122 are attached to the back face of the upper face 12a of the apparatus main body 12 so that the bottom side of the sliding groove 24 is covered.

The supporting member 122 is provided extended along an extending direction of the sliding groove 24. The supporting member 122 includes a base portion 122a formed along the upper face 12a of the apparatus main body 12, a folding portion 122b folded downward in a right angle from the tip of the base portion 122a, and a tip portion folded in a right angle from the bottom edge of the folded portion 122b. The pair of supporting members 122 are attached so that the tip portion 122c face each other. The supporting member 122 is attached to the back side of the upper face 12a of the apparatus main body 12 by fixing the base portion 122a to the back side of the upper face 12a of the apparatus main body 12 with the screw B. Here, a gap 241 is formed so that a line C can pass between the pair of tip portions 122c. The line C electrically connects an electronic circuit substrate stored in the apparatus main body 12 and the display panel 16, and is composed of, for example, a flexible substrate (FPC). A pair of flexible blocking members 123 are passed through the gap 241 and attached to the bottom face of each tip portion 122c. For example, the blocking member 123 is formed from a PET (Polyethylene terephthalate) resin film, and is provided extending along the extending direction of the sliding groove 24. The pair of blocking members 123 are provided so that the tip portion are in contact with each other. Since the blocking member 123 are composed as described above, the blocking member 123 can hold the line C inserted through the gap 241 as well as block the gap 241. Since the blocking member 123 has flexibility, the line C is able to move along the extending direction of the sliding groove 24.

The sliding base 26 as the sliding member is formed in a box shape and flanges 26a are formed projecting to the side on the lower portion of the left and right side face. The sliding base 26 is stored in the sliding groove 24 and is provided so that the bottom face is covered by the supporting member 122. Here, the flange 121 of the apparatus main body 12 and the flange 26a of the sliding base 26 are provided to be opposite each other in the up and down direction. With this, the sliding base 26 is able to slide along the sliding groove 24 without falling out from the sliding groove 24. A supporting portion 26*b* is formed by cutting out the center of the upper face of the sliding base 26 in a cylinder shape. The sliding base 26 rotatably supports the rotating shaft 34 with the supporting portion 26*b*. The rotating shaft 34 is formed in a tube shape. An inserting hole 26*c* is opened from the center of the base of the supporting portion 26*b* so that the line C can be inserted through. The inside of the rotating shaft 34 and the inserting hole 26*c* are connected to each other. Therefore, the line C inserted through the gap 241 can be guided through the inserting hole 26*c* and the inside of the rotating shaft 34 to the display panel 16.

As shown in FIG. 7, an engaging concave portion 26*d* is formed on the side face of a flange 26*a* provided on the right side face of the sliding base 26. An engaging member 124 which engages to the engaging concave portion 26*d* is attached to a predetermined position of the upper face 12*a* of the apparatus main body 12 facing the sliding groove 24. The engaging member 124 includes a flexible arm 124*a* which can be deformed and an engaging portion 124*b* which swells to the sliding groove 24 side and is formed as one with the arm 124*a* at the tip of the arm 124*a*. The arm 124*a* is biased to the sliding groove 24 side and when the sliding base 26 is slid and the engaging portion 124*b* is pressed by the side face of the flange 26*a*, the arm 124*a* flexibly deforms against the bias force. Then, as for the engaging member 124, when the position of the engaging portion 124*b* matches to the position of the engaging concave portion 26*d*, the flexibly deformed arm 124*a* returns to its shape and the engaging portion 124*b* is engaged to the engaging concave portion 26*d*. With this, it is slightly difficult for the sliding base 26 to slide and positioning of the lid 14 becomes easier.

According to the present embodiment, as described above, the configuration includes the sliding groove 24 and the sliding base 26 so that the lid 14 is able to slide in the front and back direction. Alternatively, the lid 14 does not have to slide.

As described above, according to the present embodiment, an ultrasound probe P for transmitting and receiving the ultrasound is connected to the ultrasound image diagnostic apparatus 10. The bottom edge portion of the lid 14 including the display panel 16 is connected to the apparatus main body 12 with the hinge 30, and the lid 14 can be overlapped on the apparatus main body 12 to fold the ultrasound image diagnostic apparatus 10. In the ultrasound image diagnostic apparatus 10, the hinge 30 is provided on the upper face at the near side than the center of the apparatus main body 12. The ultrasound image diagnostic apparatus 10 can be folded by rotating the lid 14 to the far side of the apparatus main body 12 with the horizontal axis H of the hinge 30 as the supporting axis. As a result, since the display panel 16 is positioned in the near side, for example, even if the apparatus is provided in a position higher than the line of view of the patient or the user such as the physician, and the ultrasound diagnostic image is viewed from below the apparatus while performing diagnosis, the display state of the display panel 16 can be easily viewed and the visibility of the display panel is enhanced.

According to the present embodiment, the hinge 30 is a biaxial hinge further including a vertical axis vertical to the horizontal axis H, and the lid 14 is able to rotate with the vertical axis V as the supporting axis. With this, the apparatus can be put away without exposing the display panel. Therefore, the display panel can be protected.

According to the present embodiment, the display panel 16 is a touch panel. Therefore, the display panel is provided near the hand, and the display panel can be touched and operated with the hand supported by the base of the apparatus. Therefore, the operability of the apparatus can be enhanced.

According to the present embodiment, the ultrasound image diagnostic apparatus 10 includes a sliding base 26 with the hinge 30 attached and the sliding groove 24 which guides the sliding base 26 to slide in the front and back direction of the upper face 12*a* of the apparatus main body 12. Therefore, the second housing can be suitably moved forward and backward to the position where the display panel can be easily viewed, and the convenience is enhanced.

According to the present embodiment, the ultrasound image diagnostic apparatus 10 includes an operating region 18 provided with at least one operating member which can be operated by the user on the near side than the hinge 30 of the apparatus main body 12. The gripping hole 20 through which the hand of the user can be inserted is opened in the operating region 18. The gripping portion 22 is formed so that the front edge portion of the apparatus main body 12 can be gripped. With this, compared to providing a gripping portion 22 which projects out from the apparatus main body, the apparatus can be made more compact, and the apparatus can be made smaller.

The description of the embodiment of the present invention is one example of the ultrasound image diagnostic apparatus, and the present invention is not limited to the above. The detailed configuration and the detailed operation of each functional unit of the ultrasound image diagnostic apparatus can be suitably changed.

According to the present embodiment, the lid 14 can be slid in the front and back direction with the sliding groove 24 and the sliding base 26 guided to slide along the sliding groove 24. However, the configuration is not limited to the above as long as the lid 14 can be guided to be able to move in the front and back direction. For example, a guiding projection can be provided on the upper face 12*a* of the apparatus main body 12 to project extending in the front and back direction. The sliding base can move on the upper face 12*a* guided by the guiding projection and with this, the lid 14 can move in the front and back direction. The shape of the sliding groove 24 and the sliding base 26 is not limited to the shape described above and a suitable shape can be applied.

According to the present embodiment, the lid 14 is able to move in the front and back direction. Alternatively, a configuration in which the lid 14 does not move is possible.

Second Embodiment

The ultrasound image diagnostic apparatus of the second embodiment is described with reference to FIG. 8 to FIG. 22. The same reference numerals are applied to the configurations the same as the first embodiment.

Figure 8:
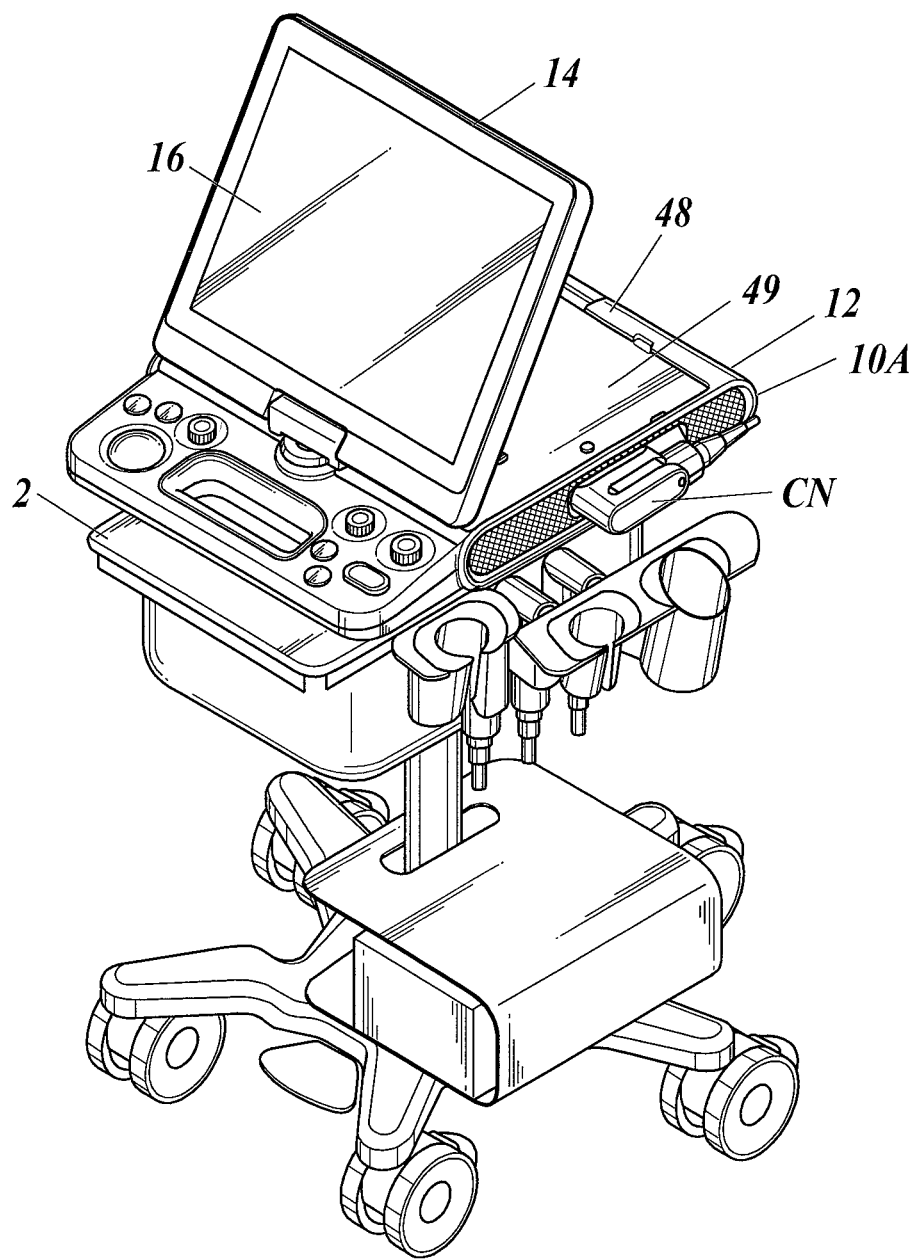
FIG. 8 is a perspective view showing an exterior appearance of the ultrasound image diagnostic apparatus of the second embodiment.

As shown in FIG. 8, the ultrasound image diagnostic apparatus 10A used as an example of the portable ultrasound image diagnostic apparatus is mounted on wheels 2, and can be moved freely to where diagnosis is performed.

The ultrasound image diagnostic apparatus 10A includes a thin box shaped apparatus main body 12, and a lid 14 which covers one face of the apparatus main body 12 and which can open and close with respect to the apparatus main body 12. A connector CN of an ultrasound probe (not shown) is connected to a connector of the apparatus main body 12 through a cable.

Figure 9:
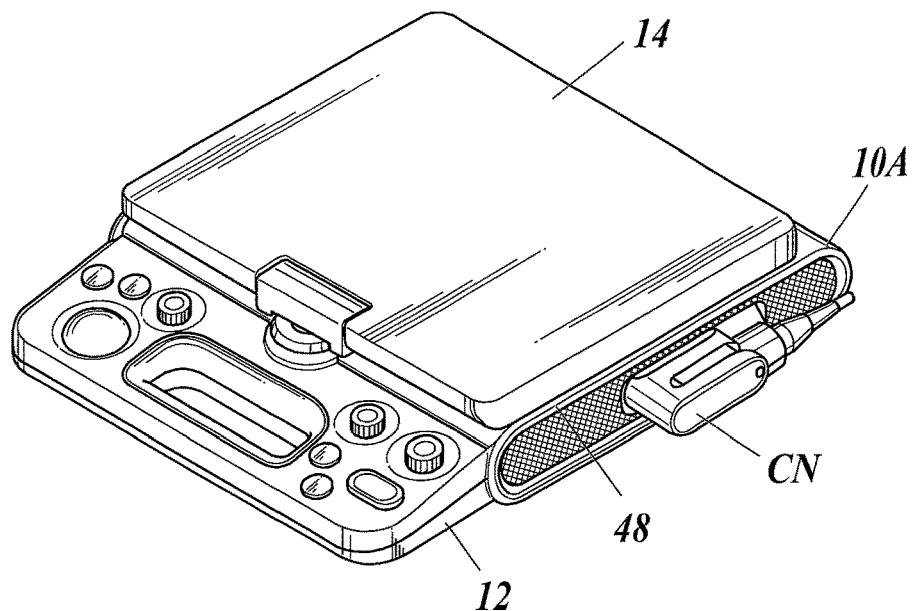
FIG. 9 is a perspective view showing an example of an operating state of a lid.
Figure 12:
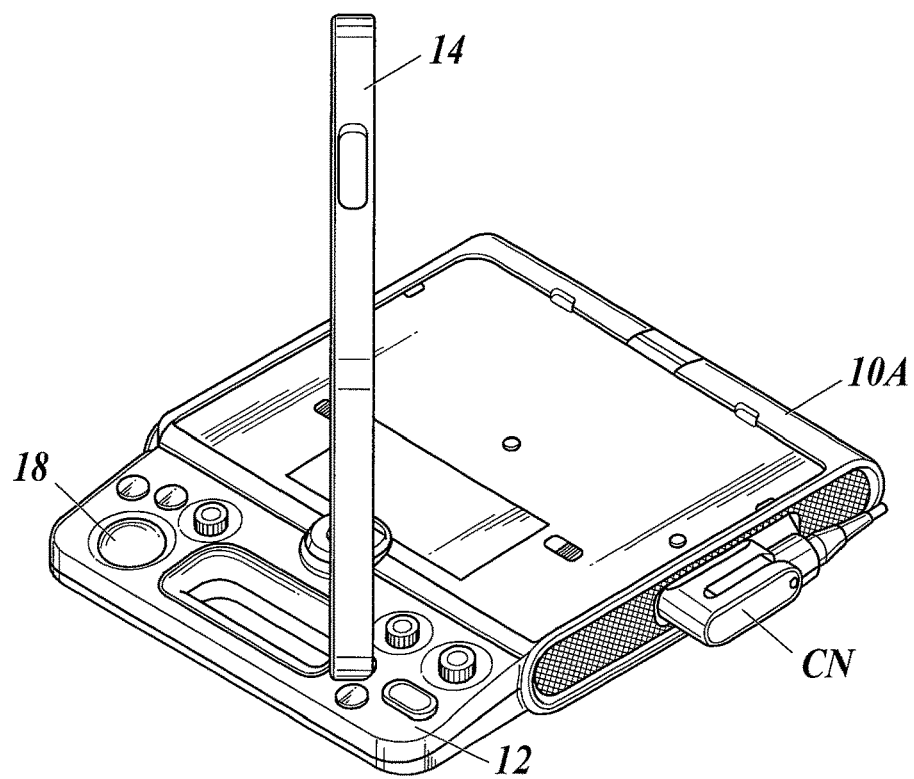
FIG. 12 is a perspective view showing an example of an operating state of the lid.
Figure 13:
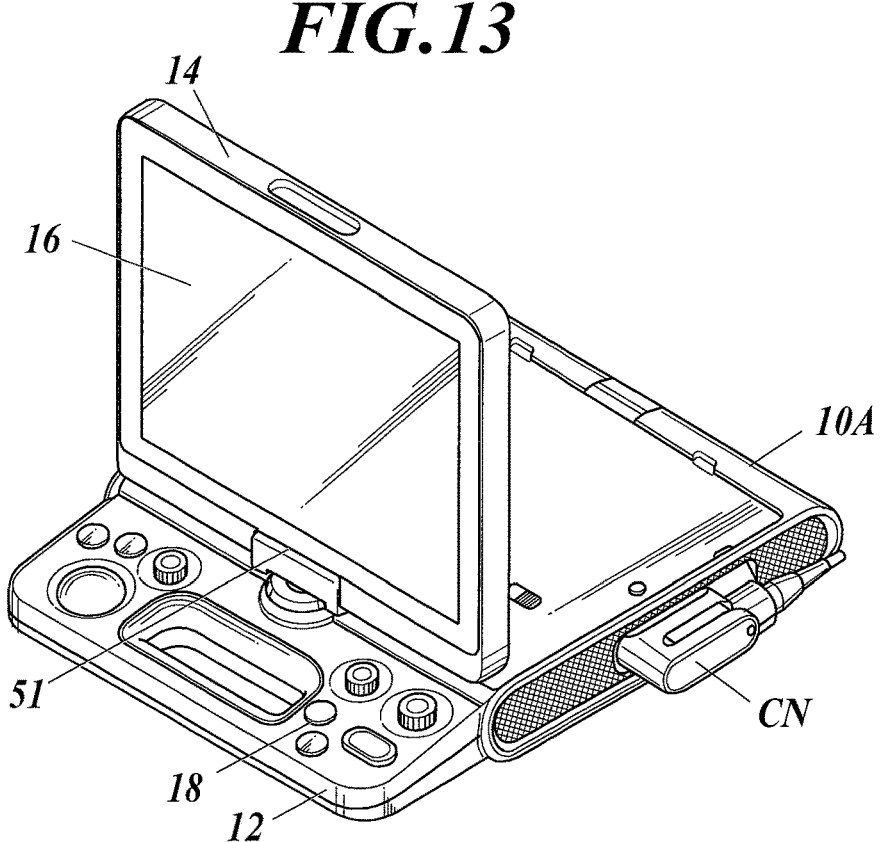
FIG. 13 is a perspective view showing an example of an operating state of the lid.
Figure 14:
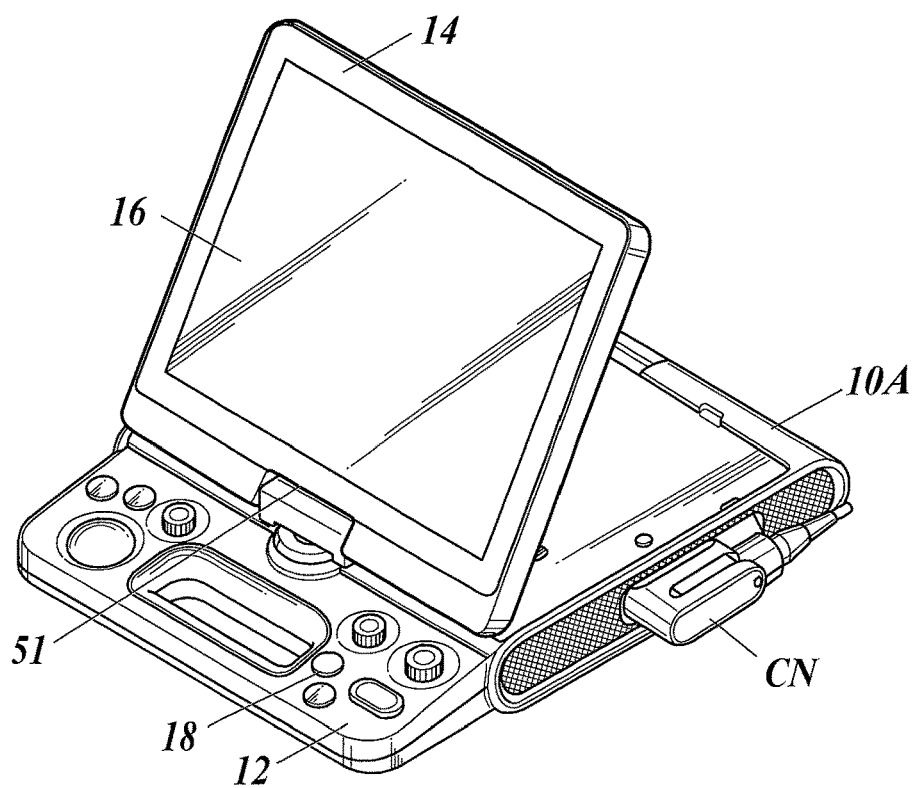
FIG. 14 is a perspective view showing an example of an operating state of the lid.

When the lid 14 is not used, as shown in FIG. 9, the lid 14 is closed toward an upper face (an example of one face) of the apparatus main body 12. When the lid 14 is used, the lid 14 is gradually opened from the state shown in FIG. 10 to the state shown in FIG. 11. Then, the lid 14 is rotated as shown in FIG. 12 and FIG. 13, and a display panel 16 is able to face the direction of an operation region 18 provided on the upper face of the apparatus main body 12. From the state in FIG. 13, the lid 14 can be tilted backward as shown in FIG. 14 so that the display panel 16 is in a state that can be easily viewed when the operation region 18 is operated. Moreover, the lid 14 can be pushed backwards from the state shown in FIG. 14, and the lid 14 can be used in a horizontal state on the upper face of the apparatus main body 12.

Figure 15:
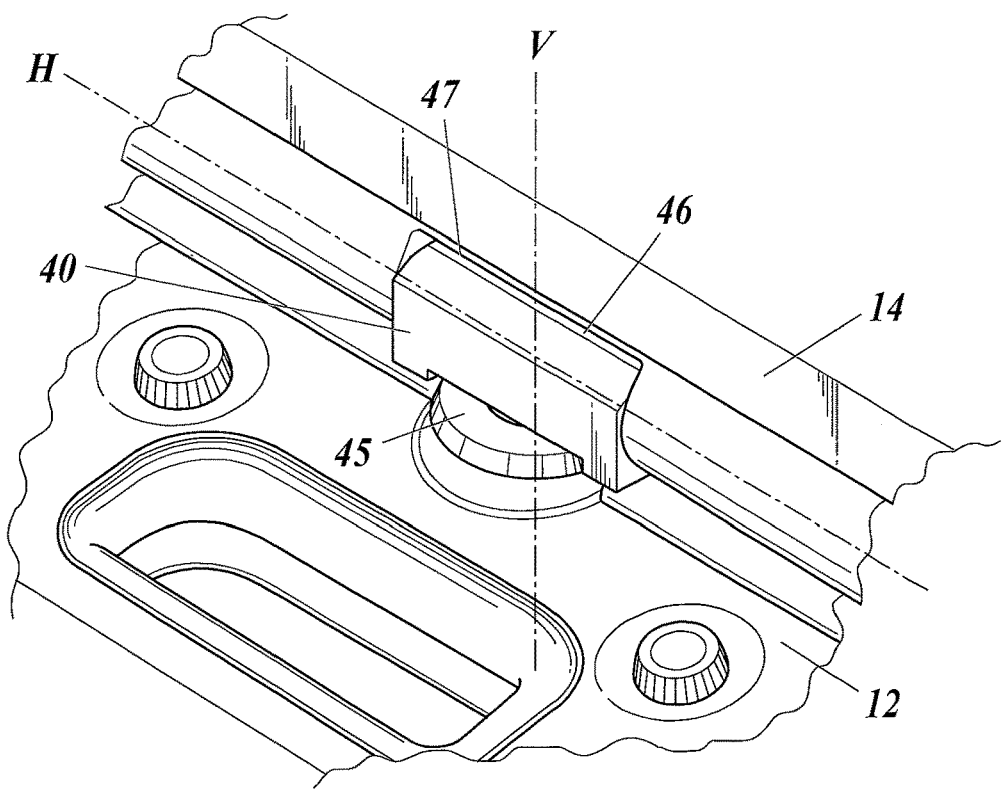
FIG. 15 is a partial enlarged perspective view showing an example of an operating state of the lid.
Figure 16:
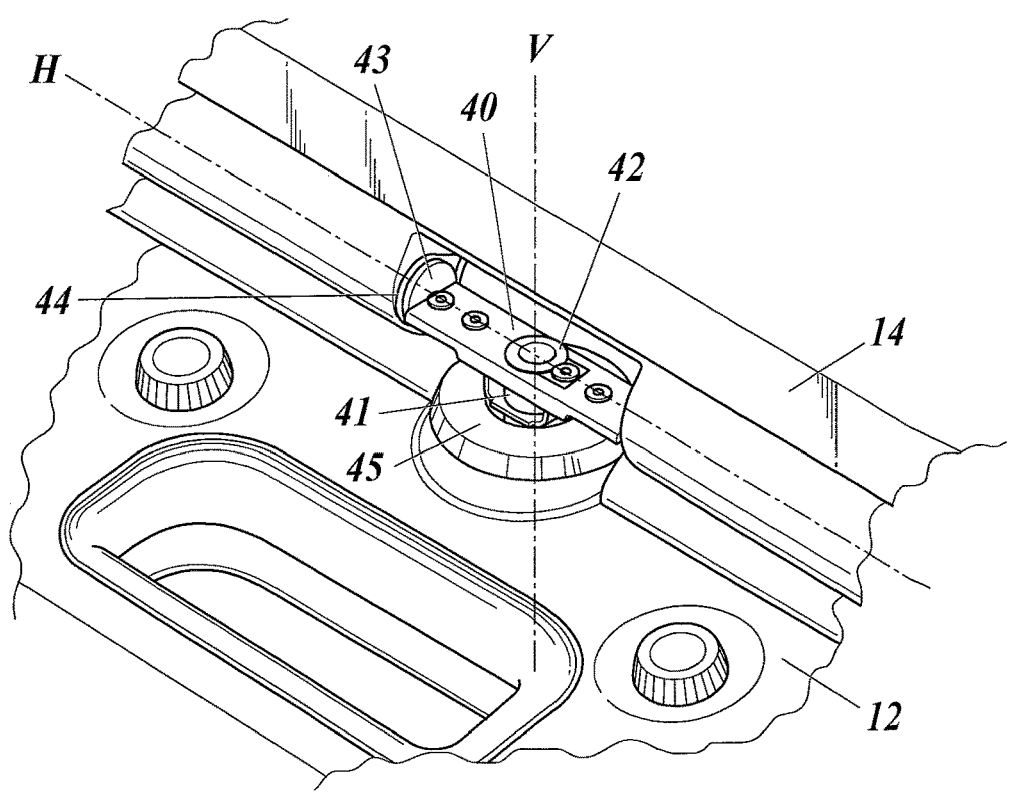
FIG. 16 is a partial enlarged perspective view showing an example of an operating state of the lid.

It is possible to understand from the above description that the lid 14 can be opened and closed and rotated with respect to the apparatus main body 12. According to the present embodiment, as shown in FIG. 15 and FIG. 16, a hinge 40 is provided on a face on the lid 14 side of the apparatus main body 12 so that the lid 14 can open, close, and rotate. FIG. 15 is a diagram showing a region near the connecting portion between the apparatus main body 12 and the lid 14 enlarged. FIG. 16 is a diagram showing the cover of the hinge 40 in FIG. 15 taken off. The hinge 40 includes a rotating shaft 42 supported by a bearing 41 provided in the apparatus main body 12, and with this, the lid 14 is able to rotate around the vertical axis V shown in FIG. 16 as the center.

Moreover, an opening/closing shaft 43 to open and close around the horizontal axis H shown in FIG. 16 as the center is provided in one of the hinge 40 or the lid 14, and the bearing 44 of the opening/closing shaft 43 is provided in the other of the hinge 40 or the lid 14.

Figure 11:
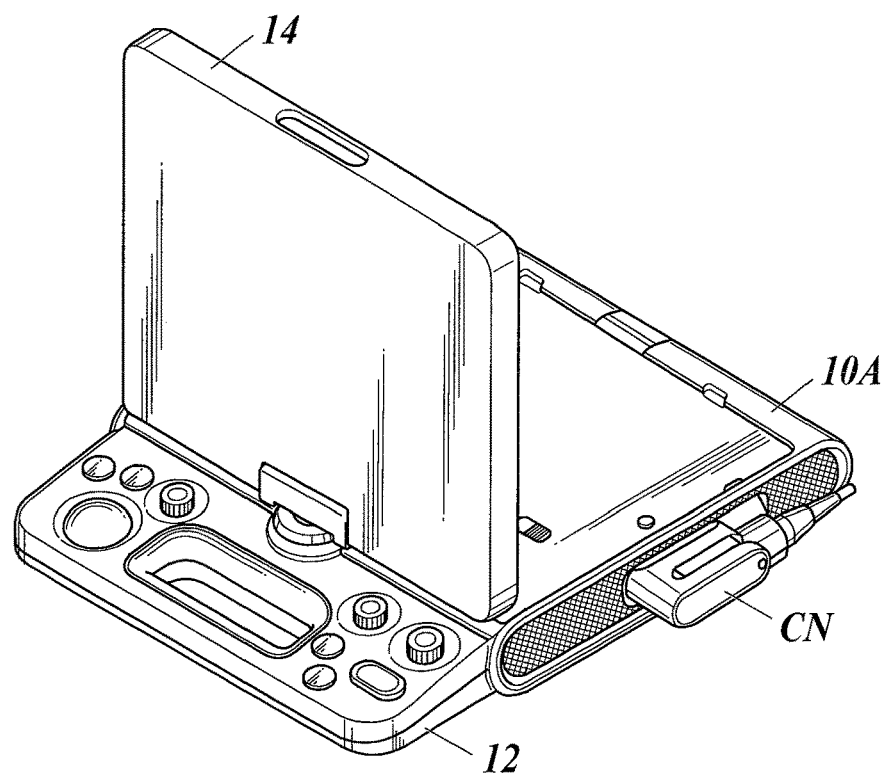
FIG. 11 is a perspective view showing an example of an operating state of the lid.

Therefore, when the lid 14 is opened from the state shown in FIG. 9 to the state shown in FIG. 11, or closed from the state shown in FIG. 13 to the state shown in FIG. 14, the lid 14 is opened and closed around the horizontal axis H shown in FIG. 16 as the center. When the lid 14 is rotated as shown in FIG. 12 or FIG. 13 from the state shown in FIG. 11, the lid 14 is rotated around the vertical axis V shown in FIG. 16 as the center.

Figure 17:
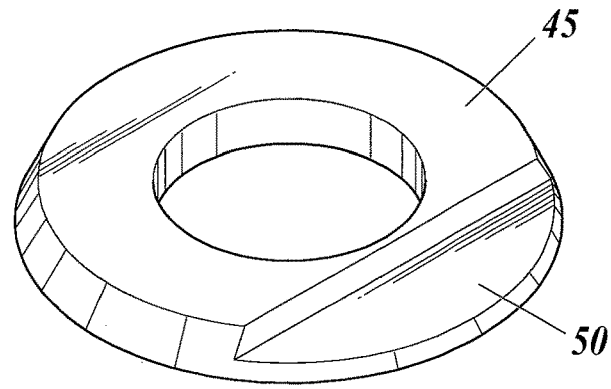
FIG. 17 is a perspective view showing an example of a damage preventing body of the ultrasound image diagnostic apparatus.
Figure 18:
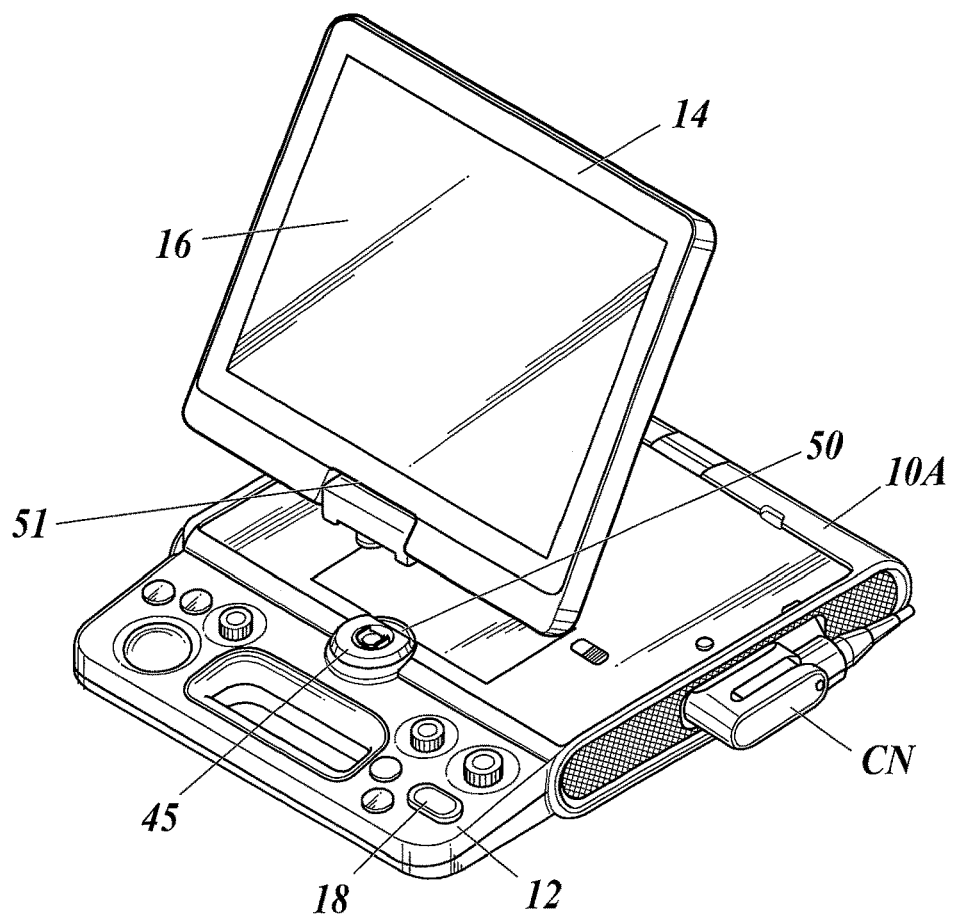
FIG. 18 is an exploded perspective view showing an example of the ultrasound image diagnostic apparatus.

The feature of the present embodiment in such configuration is that a ring shaped damage preventing body 45 as shown in FIG. 17 is provided in the outer circumference portion of the rotating shaft 42 composing the hinge 40. When the lid 14 is tilted in the state other than the closed position, the ring shaped damage preventing body 45 comes into contact with the outer peripheral portion of the lid 14. FIG. 18 is a diagram showing the ring shaped damage preventing body 45 shown in FIG. 17 provided on the apparatus main body 12. FIG. 18 is an exploded view with the lid 14 taken off so that it is possible to understand the position of the damage preventing body 45.

Figure 10:
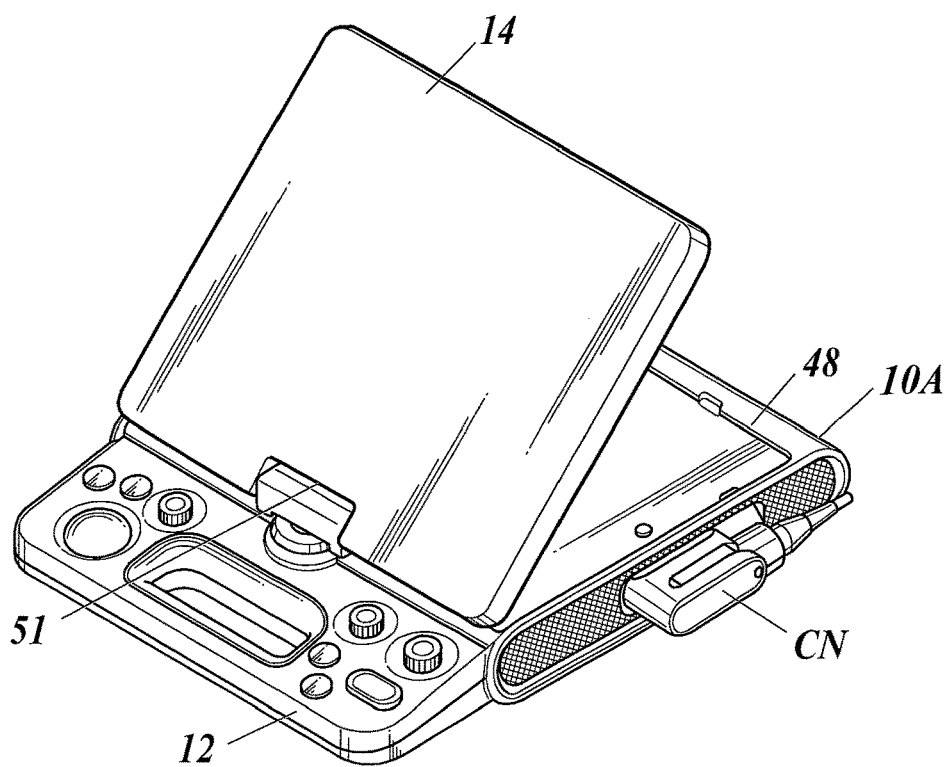
FIG. 10 is a perspective view showing an example of an operating state of the lid.

According to the present embodiment, the closed position of the lid 14 is the position where the lid 14 is tilted toward the upper face of the apparatus main body 12 from the state shown in FIG. 10 to the state shown in FIG. 9 or from the state shown in FIG. 13 to the state shown in FIG. 14 to close the lid 14.

When the lid 14 is in a position other than the above, the lid 14 cannot be tilted up or down in a predetermined value or more.

Figure 19:
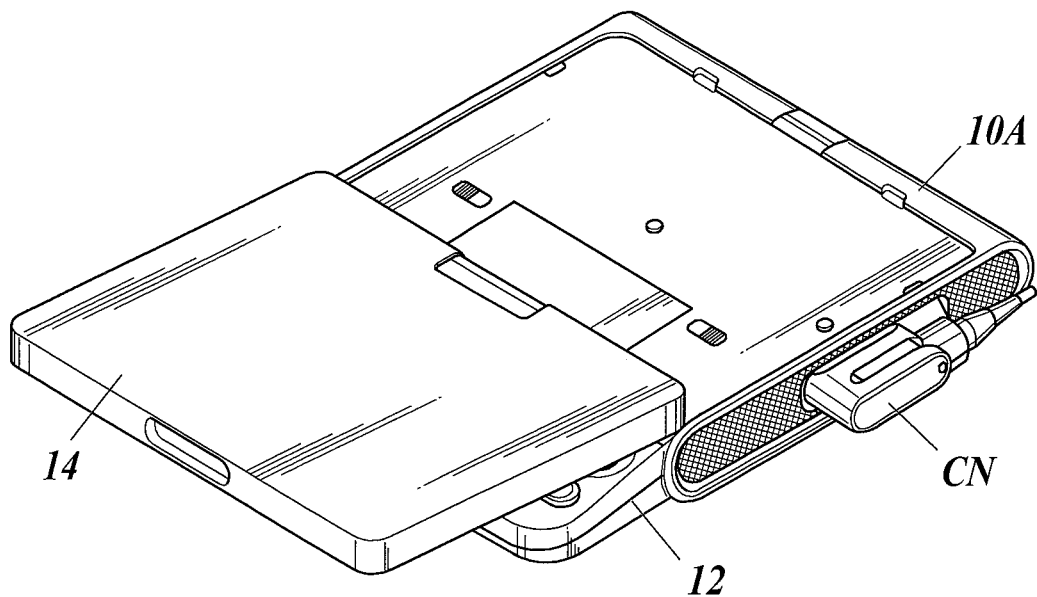
FIG. 19 is a perspective view showing an example of an operating state of the lid.
Figure 20:
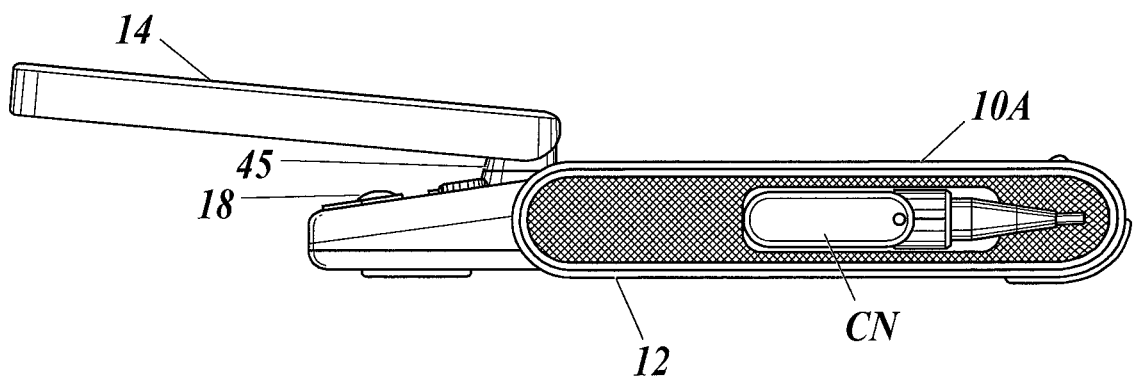
FIG. 20 is a side view showing an example of an operating state of the lid.

For example, FIG. 19 and FIG. 20 show a state where the display panel 16 of the lid 14 is tilted downward toward the operation region 18 side. FIG. 20 is a diagram viewing the ultrasound image diagnostic apparatus shown in FIG. 19 from the side. It is possible to understand from FIG. 20 that even if the lid 14 is tilted downward in the position shown in FIG. 19 and FIG. 20, the feature of the present embodiment is the display panel 16 of the lid 14 stops before hitting the upper face of the operation region 18. Therefore, according to the present embodiment as shown from FIG. 15 to FIG. 18, the ring shaped damage preventing body 45 as shown in FIG. 17 is provided in the outer circumferential portion of the rotating shaft 42 composing the hinge 40. The damage preventing body 45 comes into contact with the outer peripheral portion of the lid 14 when the lid 14 is tilted from the position other than the closed position of the lid 14. Here, according to the present embodiment as shown in FIG. 15, a storing portion 46 which stores the hinge 40 is provided on one edge of the lid 14 on the apparatus main body 12 side. Then, in the storing portion 46, an edge 47 opposite of the damage preventing body 45 with respect to the horizontal axis H is a straight line shape. The distance between the edge 47 and the horizontal axis H is made shorter than the distance from the horizontal axis H to the outer peripheral edge of the damage preventing body 45. Therefore, as shown in FIG. 20, when the display panel 16 of the lid 14 is tilted downward toward the operation region 18 side, the edge 47 which is the outer peripheral edge of the lid 14 comes into contact with the upper face of the damage preventing body 45, and the lid 14 cannot be tilted downward any further. In other words, in the state as shown in FIG. 19 and FIG. 20, it is possible to prevent the display panel 16 of the lid 14 from hitting the operation region 18, and as a result, it is possible to prevent the damage of the lid 14.

Figure 21:
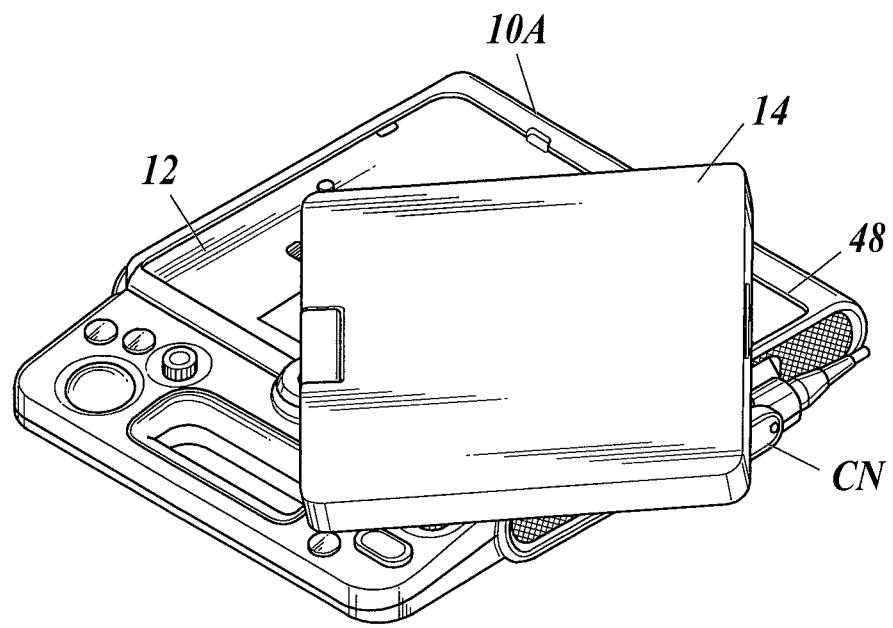
FIG. 21 is a perspective view showing an example of an operating state of the lid.
Figure 22:
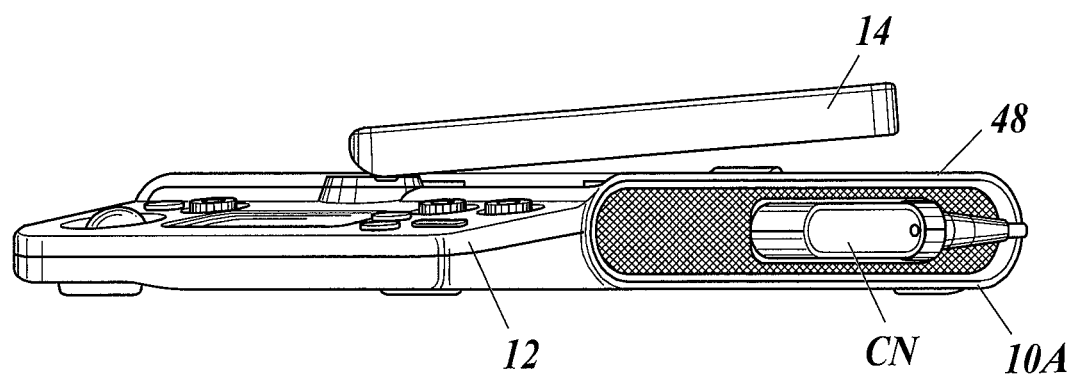
FIG. 22 is a side view showing an example of a damage preventing body of the lid.

Described next is the case where the lid 14 is tilted downward accidentally after using the lid 14 in the position shown in FIG. 12. In other words, for example, when the image on the display panel 16 of the lid 14 is shown to the patient going through ultrasound image diagnosis, the lid 14 is in a state as shown in FIG. 12. After the lid 14 is used as described above, normally the lid 14 is rotated to the state as shown in FIG. 11 and then closed as shown in FIG. 9. However, if the lid 14 is tilted downward from the state shown in FIG. 12 without rotating the lid 14 to the state shown in FIG. 11, the lid 14 becomes a state as shown in FIG. 21 or FIG. 22. FIG. 22 is a diagram of the ultrasound image diagnostic apparatus shown in FIG. 21 viewed from the side. According to the present embodiment as can be understood from FIG. 9, FIG. 10, and FIG. 21, an outer peripheral wall 48 is provided on the outer periphery of the upper face of the apparatus main body 12 to cover the outer periphery of the lid 14 excluding the hinge 40 side when the lid 14 is in a closed state. In other words, when the ultrasound image diagnostic apparatus 10A is moved to the diagnosis location placed on the wheels 2 as shown in FIG. 8, if the lid 14 is in the opened state, a main body storing unit 49 surrounded by the outer peripheral wall 48 is formed in the position on the upper face of the apparatus main body 12 where the lid 14 is in the closed state. Therefore, the ultrasound image diagnostic apparatus 10A on the wheels 2 can be moved to the diagnosis location with washing cotton, etc. placed in the main body storing unit 49, and the usability of the apparatus drastically increases. However, since such outer peripheral wall 48 is provided, when the lid 14 is tilted downward in the state shown in FIG. 12, there is a possibility that the display panel 16 hits the outer peripheral wall 48. According to the present embodiment, in this situation also, the drop of the lid 14 can be stopped at the state shown in FIG. 21 and FIG. 22 by the damage preventing body 45 shown in FIG. 17. In other words, the downward tilt of the lid 14 can be stopped with a gap as shown in FIG. 22 between the display panel 16 of the lid 14 and the outer peripheral wall 48. As a result, the damage to the display panel 16 of the lid 14 can be prevented.

In other words, since the damage preventing body 45 is in a ring shape, even in the state shown in FIG. 21 and FIG. 22, when the display panel 16 of the lid 14 is tilted downward toward the operation region 18 side, the edge 47 of the outer periphery of the lid 14 comes into contact with the upper face of the damage preventing body 45 and the lid 14 cannot be tilted downward any further. In the state shown in FIG. 21 and FIG. 22, it is possible to prevent the display panel 16 of the lid 14 from hitting the outer peripheral wall 48, and as a result, it is possible to prevent the damage of the lid 14.

The damage preventing body 45 is a ring shape as shown in FIG. 17, and a cutout portion 50 (one example of a shape of a portion which does not come into contact) is provided in the damage preventing body 45. As shown in FIG. 18, the cutout portion 50 is formed in the portion which is covered by the lid 14 when the lid 14 is in the closed state.

As shown in FIG. 15, a storing portion 46 is provided on the apparatus main body 12 side of the lid 14. The edge 47 opposite of the damage preventing body 45 with respect to the horizontal axis H has a shape in a straight line, and the straight edge 47 comes into contact with the upper face of the damage preventing body 45. Therefore, the inner side of the cutout portion 50 (the rotating shaft 42 side than the outer periphery of the damage preventing body 45) also has a straight line shape as shown in FIG. 17 and FIG. 18 to match the shape of the straight edge 47. When the lid 14 is in a closed state, the portion of the damage preventing body 45 covered by the lid 14 is to be the cutout portion 50, and the straight line shape of the cutout portion 50 becomes parallel to the edge 47.

Therefore, in the closed position of the lid 14 as shown in FIG. 9 and FIG. 10, even if the lid 14 is tilted downward (closed), the edge 47 which is the outer peripheral edge of the lid 14 does not come into contact with the upper face of the cutout portion 50, and as a result, the lid 14 can be closed as shown in FIG. 9.

The damage preventing body 45 is formed with a material softer than an outer peripheral frame 51 (portion including the edge 47) provided in the outer peripheral portion of the display panel 16 of the lid 14.

Specifically, the damage preventing body 45 is formed from rubber or synthetic resin, specifically polyacetal resin. The outer peripheral frame 51 of the lid 14 is formed from metal.

As described above, according to the present embodiment, the ultrasound image diagnostic apparatus 10A is provided with a hinge on a face of the apparatus main body on the lid side. An opening/closing shaft is provided in one of the hinge or the lid, and a bearing of the opening/closing shaft is provided in the other of the hinge or the lid. Further, a ring shaped damage preventing body composes the hinge and is provided in an outer peripheral portion of the rotating shaft in which a portion of the rotating shaft is inserted in the apparatus main body. When the lid is tilted from a state other than the closing position of the lid, the damage preventing body comes into contact with the outer peripheral portion of the lid. With this, even if the lid is opened and then the lid is tilted downward in a rotated state, it is possible to prevent the lid from being damaged.

In other words, according to the present embodiment, the outer peripheral portion of the rotating shaft composing the hinge is provided with a ring shaped damage preventing body which comes into contact with the outer peripheral portion of the lid when the lid is tilted from a state other than the closing position of the lid. Therefore, even if the lid is opened and then the lid is tilted downward in a rotated state, the outer peripheral portion of the lid comes into contact with the damage preventing body and further tilting is prevented. With this, it is possible to prevent the lid from bumping into other material and being damaged.

The details such as the specific configuration and positioning shown in the above embodiment can be suitably changed without leaving the scope of the present invention.

The entire disclosure of Japanese Patent Application No. 2013-239506 filed on Nov. 20, 2013 and Japanese Patent Application No. 2013-266804 filed on Dec. 25, 2013 including description, claims, drawings, and abstract are incorporated herein by reference in its entirety.

What is claimed is:

1. A portable ultrasound image diagnostic apparatus comprising:
   a first housing including an upper face, a lower face opposite the upper face along a first direction, and plural side faces, the upper, lower, and side faces of the first housing having a fixed positional relationship with respect to each other, and the lower face of the first housing opposing a surface on which the portable ultrasound apparatus is placed during use;
   a second housing including a display panel, the display panel including a touch panel;
   a single sliding groove along which the second housing is slidable with respect to the first housing across the upper face of the first housing;
   an ultrasound probe which comprises a cable and which transmits and receives ultrasound;
   a connector comprising a hinge mechanism having a horizontal axis, the connector connecting the first housing and a lower portion of the second housing, and the connector being provided on the upper face of the first housing at a position such that the horizontal axis of the hinge mechanism is forward of a center of the upper face of the first housing in a direction toward a front side of the first housing, the upper face of the first housing including a first portion provided between the connector and a rear side of the first housing; and
   a terminal to which the ultrasound probe is connectable via the cable, the terminal being provided on the first housing,
   wherein:
   the hinge mechanism is attached to a sliding base of the single sliding groove;
   the connector connects the first housing and the lower portion of the second housing such that the second housing is rotatable about the horizontal axis of the hinge mechanism within an entirety of a range from (i) a first position at which an angle between the first portion of the upper face of the first housing and the second housing is substantially 0 degrees, to (ii) a second position at which the angle between the first portion of the upper face of the first housing and the second housing is substantially 90 degrees, the second housing being put in a closed state from an opened state by rotating the second housing towards the rear side of the first housing until the second housing is in the first position,
   an operating region provided with at least one operating member which is operable by a user is provided in the first housing, the operating region being provided between the connector and the front side of the first housing,
   when the second housing is in the closed state, an entirety of an area of the second housing that opposes the display panel (i) also opposes the first portion of the upper face of the first housing along the first direction, and (ii) does not oppose the operating region along the first direction, the display panel is capable of being exposed when the second housing is in the closed state, a gripping portion is provided in the operating region, the gripping portion comprising a gripping hole into which a hand of the user is insertable to allow the user to grip a front edge portion of the first housing, and the terminal is provided on one face from among the plural side faces of the first housing at a position that is closer to the rear side of the first housing than to the front side of the first housing.

2. The portable ultrasound image diagnostic apparatus of claim 1, wherein the connector comprises a biaxial hinge further including a vertical axis vertical to the horizontal axis, the second housing being rotatable with the vertical axis as a supporting axis.

3. The portable ultrasound image diagnostic apparatus of claim 1, wherein the single sliding groove is provided in the upper face of the first housing and guides the sliding member in a front and back direction of the upper face of the first housing.

4. The portable ultrasound image diagnostic apparatus of claim 1, wherein:

the second housing is rotatable by a rotating shaft with respect to the first housing when the second housing is in the opened state, the opened state being a state in which the second housing is not in the closed state, and a damage preventing body having a ring shape is provided in an outer peripheral portion of the rotating shaft, wherein a part of the rotating shaft is inserted inside the first housing and the damage preventing body comes into contact with an outer peripheral portion of the second housing when the second housing is tilted from a state other than the closed state.

5. The portable ultrasound image diagnostic apparatus of claim 4, wherein a cutout portion is provided in the damage preventing body.

6. The portable ultrasound image diagnostic apparatus of claim 5, wherein the lower portion of the second housing includes a straight line portion, and the cutout portion has a shape such that the straight line portion does not come into contact with the cutout portion when the second housing is in the closed position.

7. The portable ultrasound image diagnostic apparatus of claim 6, wherein a portion of an edge of the cutout portion is a straight line.

8. The portable ultrasound image diagnostic apparatus of claim 4, wherein the damage preventing body is formed from a material softer than a material of an outer peripheral frame provided at the outer peripheral portion of the second housing.

9. The portable ultrasound image diagnostic apparatus of claim 8, wherein the damage preventing body is formed from rubber or synthetic resin and the outer peripheral frame of the second housing is formed from metal.

10. The portable ultrasound image diagnostic apparatus of claim 4, wherein a storing portion which stores the hinge mechanism is provided in the lower portion of the second housing.

11. The portable ultrasound image diagnostic apparatus of claim 1, wherein the one face is a right side face of the first housing.

12. The portable ultrasound image diagnostic apparatus of claim 1, wherein the gripping portion is provided in the operating region at a position adjacent to the connector.

13. A portable ultrasound image diagnostic apparatus comprising:

a first housing including an upper face, a lower face opposite the upper face along a first direction, and plural side faces, the upper, lower, and side faces of the first housing having a fixed positional relationship with respect to each other, and the lower face of the first housing opposing a surface on which the portable ultrasound apparatus is placed during use;

a second housing including a display panel, the display panel including a touch panel;

a single sliding groove along which the second housing is slidable with respect to the first housing across the upper face of the first housing;

an ultrasound probe which comprises a cable and which transmits and receives ultrasound;

a connector comprising a hinge mechanism having a horizontal axis, the connector connecting the first housing and a lower portion of the second housing, and the connector being provided on the upper face of the first housing at a position such that the horizontal axis of the hinge mechanism is forward of a center of the upper face of the first housing in a direction toward a front side of the first housing, the upper face of the first housing including a first portion provided between the connector and a rear side of the first housing; and a terminal to which the ultrasound probe is connectable via the cable, the terminal being provided on the first housing, wherein:

the hinge mechanism is attached to a sliding base of the single sliding groove;

the connector connects the first housing and the lower portion of the second housing such that the second housing is rotatable about the horizontal axis of the hinge mechanism within an entirety of a range from (i) a first position at which an angle between the first portion of the upper face of the first housing and the second housing is substantially 0 degrees, to (ii) a second position at which the angle between the first portion of the upper face of the first housing and the second housing is substantially 90 degrees, the second housing being put in a closed state from an opened state by rotating the second housing towards the rear side of the first housing until the second housing is in the first position, an operating region provided with at least one operating member which is operable by a user is provided in the first housing, the operating region being provided between the connector and the front side of the first housing, when the second housing is in the closed state, an entirety of an area of the second housing that opposes the display panel (i) also opposes the first portion of the upper face of the first housing along the first direction, and (ii) does not oppose the operating region along the first direction, the operating region and the display panel are exposed when the second housing is in the closed state, and the terminal is provided on one face from among the plural side faces of the first housing at a position that is closer to the rear side of the first housing than to the front side of the first housing.

14. The portable ultrasound image diagnostic apparatus of claim 13, wherein a gripping portion is provided in the operating region, the gripping portion comprising a gripping hole into which a hand of the user is insertable to allow the user to grip a front edge portion of the first housing.

15. The portable ultrasound image diagnostic apparatus of claim 13, wherein the one face is a right side face of the first housing.

16. The portable ultrasound image diagnostic apparatus of claim 13, further comprising:
a gripper provided adjacent to the connector.

17. A portable ultrasound image diagnostic apparatus comprising:
a first housing including an upper face, a lower face opposite the upper face along a first direction, and plural side faces, a wall portion being provided at a rear side of the first housing on the upper face of the first housing, the upper, lower, and side faces of the first housing having a fixed positional relationship with respect to each other, and the lower face of the first housing opposing a surface on which the portable ultrasound image diagnostic apparatus is placed during use;
a second housing including a display panel, the display panel including a touch panel;
a single sliding groove along which the second housing is slidable with respect to the first housing across the upper face of the first housing;
an ultrasound probe which comprises a cable and which transmits and receives ultrasound;
a connector comprising a hinge mechanism having a horizontal axis, the connector connecting the first housing and a lower portion of the second housing, and the connector being provided on the upper face of the first housing at a position such that the horizontal axis of the hinge mechanism is forward of a center of the upper face of the first housing in a direction toward a front side of the first housing, the upper face of the first housing including a first portion provided between the connector and a rear side of the first housing; and
a terminal to which the ultrasound probe is connectable via the cable, the terminal being provided on the first housing,
wherein:
the hinge mechanism is attached to a sliding base of the single sliding groove;
the connector connects the first housing and the lower portion of the second housing such that the second housing is rotatable about the horizontal axis of the hinge mechanism within an entirety of a range from (i) a first position at which an angle between the first portion of the upper face of the first housing and the second housing is substantially 0 degrees, to (ii) a second position at which the angle between the first portion of the upper face of the first housing and the second housing is substantially 90 degrees, the second housing being put in a closed state from an open state by rotating the second housing towards the rear side of the first housing until the second housing is in the first position,
when the second housing is in the closed state, an entirety of the display panel is located between the hinge mechanism and the wall portion on the upper face of the first housing,
when the second housing is in the closed state, an entirety of an area of the second housing that opposes the display panel (i) also opposes the first portion of the upper face of the first housing along the first direction, and (ii) does not oppose an operating region along the first direction,
the display panel is capable of being exposed when the second housing is in the closed state, and
the terminal is provided on one face from among the plural side faces of the first housing at a position that is closer to the rear side of the first housing than to the front side of the first housing.

18. The portable ultrasound image diagnostic apparatus of claim 17, wherein an operating member which is operable by the user is provided between the connector and the front side of the first housing.

19. The portable ultrasound image diagnostic apparatus of claim 18, wherein the operating member is exposed when the second housing is in the closed state.

20. The portable ultrasound image diagnostic apparatus of claim 17, wherein the connector comprises a biaxial hinge further including a vertical axis vertical to the horizontal axis, the second housing being rotatable with the vertical axis as a supporting axis.

21. The portable ultrasound image diagnostic apparatus of claim 17, wherein the one face is a right side face of the first housing.

22. The portable ultrasound image diagnostic apparatus of claim 17, further comprising:
a gripping portion provided on the first housing, a position of the gripping portion being closer to the front side of the housing than a position of the horizontal axis of the hinge mechanism.

23. The portable ultrasound image diagnostic apparatus of claim 17, wherein an operating member which is operable by the user is provided closer to the front side of the housing than a position of the horizontal axis of the hinge mechanism.

24. The portable ultrasound image diagnostic apparatus of claim 23, wherein the operating member is exposed when the second housing is in the closed state.

25. The portable ultrasound image diagnostic apparatus of claim 17, wherein the connector comprises a torque limiter.

26. The portable ultrasound image diagnostic apparatus of claim 17, wherein the single sliding groove is provided in the upper face of the first housing and guides the sliding member in a front and back direction of the upper face of the first housing.

27. The portable ultrasound image diagnostic apparatus of claim 17, further comprising:
a gripper provided adjacent to the connector.

\* \* \* \* \*